United States Patent [19]
Arai et al.

[11] Patent Number: 5,639,665
[45] Date of Patent: Jun. 17, 1997

[54] METHOD OF SPOTTING SAMPLE LIQUID ON DRY CHEMICAL ANALYSIS FILM

[75] Inventors: Takaki Arai; Osamu Seshimoto, both of Saitama-ken, Japan

[73] Assignee: Fuji Photo Film Co., Ltd., Kanagawa-ken, Japan

[21] Appl. No.: 568,475

[22] Filed: Dec. 7, 1995

[30] Foreign Application Priority Data

Dec. 20, 1994 [JP] Japan .................................. 6-316339

[51] Int. Cl.⁶ .................................................. G01N 35/10
[52] U.S. Cl. .................. 436/50; 436/46; 436/49; 436/54; 436/55; 436/174; 436/180; 422/63; 422/66; 422/67; 422/100
[58] Field of Search .................... 436/43, 44, 46, 436/47, 48, 49, 50, 54, 55, 174, 180; 422/63, 64, 67, 68.1, 81, 100, 105, 66; 141/130, 351, 352, 251, 258, 260, 263

[56] References Cited

U.S. PATENT DOCUMENTS

| | | | |
|---|---|---|---|
| 4,340,390 | 7/1982 | Collins et al. | |
| 4,452,899 | 6/1984 | Alston | 436/46 |
| 5,081,038 | 1/1992 | Sugaya et al. | 436/46 |
| 5,133,392 | 7/1992 | Hamann | 141/1 |
| 5,143,849 | 9/1992 | Barry et al. | 436/50 |
| 5,204,268 | 4/1993 | Matsumoto | 436/44 |
| 5,334,353 | 8/1994 | Blattner | |

FOREIGN PATENT DOCUMENTS

| | | |
|---|---|---|
| 0505004 | 9/1992 | European Pat. Off. |
| 0677744 | 10/1995 | European Pat. Off. |
| 2-247563 | 10/1990 | Japan |

OTHER PUBLICATIONS

Patent Abstracts of Japan, vol. 008, No. 252, Nov. 17 1984 & JP A 59 122955 (Shimazu Seuisakusho KK).

*Primary Examiner*—Long V. Le
*Attorney, Agent, or Firm*—McAulay Fisher; Nissen Goldberg & Kiel, LLP

[57] ABSTRACT

When spotting a sample liquid onto a plurality of frameless chemical analysis films, a predetermined amount of the sample liquid is sucked into a spotting tip, the lower end of the spotting tip is brought into contact with the surface of each chemical analysis film and the pressure in the spotting tip is increased to discharge the sample liquid therein onto the surface of the chemical analysis film while lifting the spotting tip away from the surface of the film. When a first chemical analysis film includes a component which can deteriorate the accuracy of measurement of the analyte for the second frameless chemical analysis film, the sample liquid is spotted, before the second chemical analysis film after the first chemical analysis film, on a third frameless chemical analysis film which does not include a component which can deteriorate the accuracy of measurement of the analyte of the second chemical analysis film and the analyte of which is not such that the accuracy of its measurement is substantially affected by a component of the first chemical analysis film which can be transferred to the third chemical analysis film.

7 Claims, 6 Drawing Sheets

METHOD OF SPOTTING SAMPLE LIQUID ON DRY CHEMICAL ANALYSIS FILM

BACKGROUND OF THE INVENTION

1. Field of the Invention

This invention relates to a method of spotting sample liquid such as blood or urine with a spotting tip onto a frameless dry (dry-to-the-touch) chemical analysis film having a reagent layer containing therein a reagent whose optical density changes by chemical reaction, biochemical reaction, immunoreaction or the like with a specific biochemical component (the object of measurement; sometimes called "analyte" or "item of object") contained in the sample liquid. More particularly, this invention relates to such a method which, when a sample liquid is to be spotted onto a plurality of frameless dry chemical analysis films for different analytes in sequence, can prevent deterioration in accuracy of measurement for frameless dry chemical analysis films which are spotted with the sample liquid later due to contamination of the spotting tip by a substance on the chemical analysis films which are spotted earlier.

2. Description of the Related Art

There has been put into practice a dry chemical analysis film (sometimes referred to as "multi-layered chemical analysis element") with which a specific biochemical component or the like contained in a sample liquid can be quantitatively analyzed through a droplet of the sample liquid spotted onto the chemical analysis film. When a biochemical component or the like contained in a sample liquid is quantitatively analyzed using such a chemical analysis film, a droplet of the sample liquid is spotted onto the chemical analysis film and is held at a constant temperature for a predetermined time (incubation) in an incubator to cause coloring reaction. Then measuring light containing a wavelength which is pre-selected according to the combination of the component to be analyzed and the reagent contained in the reagent layer of the chemical analysis film is projected onto the chemical analysis film and the reflective optical density of the chemical analysis film is measured. The concentration in the sample liquid of the component to be analyzed is determined on the basis of the reflective optical density using a calibration curve or a standard curve which represents the relation between the concentration of the component and the reflective optical density.

The dry chemical analysis film comprises a support sheet such as of a plastic sheet and a reagent layer which contains a reagent and is formed on the support sheet. Conventionally the chemical analysis film is generally used in the form of a chemical analysis slide comprising a chip of the chemical analysis film held by an organic polymer or a plastic frame.

However use of such chemical analysis films with frame results in increase in the sizes of various parts handling the films such as cells in the incubator for incubating the films, the transfer system, a film supplier for storing the films in dry state, a chemical analysis film cartridge and the like. Thus the frame of the chemical analysis slide is obstructive to reducing the size of the biochemical analysis apparatus and at the same time reduces the film accommodating capacity of the incubator and the film supplier, which obstructs increase in the overall throughput capacity of the biochemical analysis apparatus. Further cost for mounting the frame is high and adds to cost of biochemical analysis.

In view of these circumstances, we have previously proposed a system of biochemical analysis in which a chip of chemical analysis film as it is or without film is used. The chemical analysis film chip without frame will be referred to as "frameless chemical analysis film" in order to distinguish it from the chemical analysis slide, i.e., the chemical analysis film chip with frame, hereinbelow.

In the case of a chemical analysis slide, the sample liquid is spotted in the following manner. That is, after a droplet of the sample liquid is formed at the end of the spotting tip, the spotting tip is lowered toward the surface of the slide and is stopped when the droplet is brought into contact with the chemical analysis film of the slide, thereby causing the droplet to spread over the surface of the film.

In the method described in U.S. Pat. No. 4,340,390, the lower end of the spotting tip is stopped at a predetermined distance from the surface of the film and then the sample liquid in the spotting tip is discharged at a predetermined rate.

However when such methods of spotting the sample liquid on the chemical analysis slide are used for the frameless chemical analysis film, the following difficulties are encountered. That is, though in the case of chemical analysis slides in which the surface of the film is kept flat by the frame, the position of the film surface can be held constant irrespective of the kind of the chemical analysis film, the position of the film surfaces is apt to vary according to the kind of the chemical analysis film in the case of the frameless chemical analysis film since the frameless chemical analysis film is warped or curled or curved in a dry state and the degree of warp, curl or curve varies depending on the kind of the chemical analysis film.

Accordingly when the distance between the end of the spotting tip and the film surface is too large, the droplet or the discharged flow of the sample liquid is apt to break near the end of the spotting tip and part of the sample liquid is apt to remain in the spotting tip. This phenomenon is more apt to occur when the sample liquid spreads over the chemical analysis film at a high rate and when the viscosity of the sample liquid is low.

On the other hand, when the distance between the end of the spotting tip and the film surface is too small, the sample liquid stands up above the film surface and the end portion of the spotting tip dips into the sample liquid on the film surface. As a result, part of the sample liquid remains adhering to the outer surface of the end portion of the spotting tip after end of spread of the sample liquid. This phenomenon is more apt to occur when the sample liquid spreads over the chemical analysis film at a low rate and when the viscosity of the sample liquid is high.

Further in the spotting method described in U.S. Pat. No. 5,143,849, a meniscuscoid droplet is formed on the end of the spotting tip and the spotting tip is lowered toward the film. The spotting tip is stopped when that the droplet is brought into contact with the film surface is detected through a fine change in the pressure in the spotting tip, and the sample liquid in the spotting tip is discharged in this state or after the spotting tip is lifted by a predetermined amount.

With this method, the distance between the end of the spotting tip and the film surface can be precisely controlled and accordingly the problem inherent to the two prior arts described above can be avoided. However since the meniscuscoid droplet is small in size, it takes a long time to detect whether the droplet is in contact with the film surface and accordingly it is difficult to lower the spotting tip at a high speed, which makes it difficult to shorten the spotting time.

There are plurality of analytes for a sample liquid such as blood, urine or the like, and different chemical analysis films are used for the respective analytes.

When a sample liquid is spotted onto a plurality of different frameless chemical analysis films in sequence, there is a fear that accuracy of measurement can deteriorate depending on the order in which the frameless chemical analysis films are spotted with the sample liquid. That is, since it is difficult to keep constant the position of the surface of the frameless chemical analysis film, i.e., the level of a spreading layer or a blood cell filtering layer on which the sample liquid is spotted, for the reason described above, it has been proposed a method of spotting a sample liquid in which the end of the spotting tip is once brought into contact with the surface of the chemical analysis film and then the sample liquid is discharged from the spotting tip while moving upward the spotting tip in order to make constant the distance between the end of the spotting tip and the film surface, which greatly affects the accuracy of measurement. (European Unexamined Patent Publication No. 0677744)

When the spotting tip is brought into contact with the surface of the chemical analysis film, one or more of the components of the reagent layer of the chemical analysis film can adhere to the spotting tip, and since a spotting tip is used when a sample liquid is spotted onto a plurality of chemical analysis films, the component of the reagent layer of the preceding chemical analysis film adhering to the spotting tip can be transferred to the reagent layer of the next chemical analysis film through the contact between the spotting tip and the reagent layer or can be dissolved into the sample liquid and spotted onto the next chemical analysis film together with the sample liquid. When the reagent layer of the next chemical analysis film is thus contaminated, the measured concentration or activity of the specific analyte to be analyzed with the chemical analysis film can be affected by the contaminant, which can lead to a large measuring error.

For example, when the analyte for a frameless chemical analysis film is LDH (lactate dehydrogenase) and the analyte for the next frameless chemical analysis film is GPT (glutamic-pyruvic transaminase), GPT is contained in the reagent layer of the chemical analysis film for LDH and part of the GPT component can adhere to the spotting tip when the spotting tip is brought into contact with the chemical analysis film for LDH. When the GPT component adhering to the spotting tip is transferred to the chemical analysis film for GPT, the GPT component adds to the inherent GPT content (or activity) of the sample liquid, whereby the measured value of the GPT content becomes larger than the real value.

Actually, our experiment has revealed that the measured value (activity) of the GPT becomes larger than the actual value by 1.5 to 2 U/L (U represents international unit and L represents liter) when the sample liquid is spotted onto the frameless chemical analysis film for GPT with the spotting tip in contact with the film after the frameless chemical analysis film for LDH is spotted with the sample liquid with the spotting tip in contact with the film as will be described later with reference to FIGS. 7A and 7B. Since the measured value of GPT normally should be in the range of 4 to 36 U/L, increase of the measured value over the actual value by 1.5 to 2 U/L can lead to misdiagnosis that the sample liquid whose actual GPT value is 34 to 36 U/L is diseased (disease in heart, liver or bile biliary duct or malignant adenoma).

SUMMARY OF THE INVENTION

In view of the foregoing observations and description, the primary object of the present invention is to provide a method of spotting a sample liquid onto a plurality of frameless chemical analysis films which, when a sample liquid is to be spotted onto a plurality of frameless dry chemical analysis films in sequence with a spotting tip brought into contact with the surface of the films, can prevent deterioration in accuracy of measurement for frameless dry chemical analysis films which are spotted with the sample liquid later due to contamination of the spotting tip by a substance on the frameless dry chemical analysis films which are spotted earlier.

In accordance with one aspect of the present invention, there is provided a method of spotting a sample liquid onto a plurality of frameless chemical analysis films comprising the steps of sucking a predetermined amount of the sample liquid into a spotting tip onto a spotting nozzle, lowering the spotting tip to bring the lower end of the spotting tip into contact with the surface of each frameless chemical analysis film and increasing the pressure in the spotting tip to discharge the sample liquid therein onto the surface of the frameless chemical analysis film while lifting the spotting tip away from the surface of the frameless chemical analysis film, wherein the improvement comprises that when a first frameless chemical analysis film includes a component which can be transferred to a second frameless chemical analysis film by way of the spotting tip and can deteriorate the accuracy of measurement of the analyte for the second frameless chemical analysis film, the sample liquid is spotted, before the second frameless chemical analysis film after the first frameless chemical analysis film, onto a third frameless chemical analysis film which does not include a component which can be transferred to the second frameless chemical analysis film by way of the spotting tip and can deteriorate the accuracy of measurement of the analyte of the second frameless chemical analysis film and the analyte of which is not such that the accuracy of its measurement is substantially affected by a component of the first frameless chemical analysis film which can be transferred to the third frameless chemical analysis film from the first frameless chemical analysis film by way of the spotting tip.

In accordance with another aspect of the present invention, there is provided a method of spotting a sample liquid onto a plurality of frameless chemical analysis films comprising the steps of sucking a predetermined amount of the sample liquid into a spotting tip on a spotting nozzle, lowering the spotting tip to bring the lower end of the spotting tip into contact with the surface of each frameless chemical analysis film and increasing the pressure in the spotting tip to discharge the sample liquid therein onto the surface of the frameless chemical analysis film while lifting the spotting tip away from the surface of the frameless chemical analysis film, wherein the improvement comprises that when a first frameless chemical analysis film includes a component which can be transferred to a second frameless chemical analysis film by way of the spotting tip and can deteriorate the accuracy of measurement of the analyte for the second frameless chemical analysis film, the sample liquid is first spotted onto the second frameless chemical analysis film and then onto the first frameless chemical analysis film.

For example, this method is useful for a combination of lactate dehydrogenase (an analyte of the first frameless chemical analysis film) and glutamic-pyruvic transaminase (alanine aminotransferase) (an analyte of the second frameless chemical analysis film), a combination of total cholesterol and inorganic phosphorous or uric acid, a combination of glutamic-pyruvic transaminase and inorganic phosphorous or glutamic-oxaloacetic transaminase (aspartate aminotransferase), and a combination of alkaline phosphatase and γ-glutamyl transpeptitase.

In the method of the present invention, the lower end of the spotting tip is once brought into contact with the surface of the frameless chemical analysis film and then lifted away from the film surface before discharging the sample liquid, and accordingly the distance between the end of the spotting tip and the film surface upon discharge can be precisely known irrespective of variation of the level of the film surface due to variation of the degree of warp, curl or curve of the frameless chemical analysis film and irrespective of variation of position of the end of the spotting tip due to variation of the length of the spotting tip or the mounting position of the spotting tip on the spotting nozzle. Accordingly, the distance between the end of the spotting tip and the film surface upon discharging the sample liquid can be optimally controlled so that no sample liquid remains on the outer surface of or inside the spotting tip, whereby a predetermined amount of the sample liquid is surely supplied to the frameless chemical analysis film and fluctuation in accuracy of measurement can be suppressed.

Further when the sample liquid is spotted, after the first frameless chemical analysis film, onto the third frameless chemical analysis film the measured value of which cannot be affected by a component of the first frameless chemical analysis film prior to the second frameless chemical analysis film the measured value of which can be affected by a component of the first frameless chemical analysis film and then is spotted onto the second frameless chemical analysis film, the component of the first frameless chemical analysis film adhering to the spotting tip is removed to such an extent that cannot substantially affect the measurement with the second frameless chemical analysis film and accordingly the accuracy of measurement with the second frameless chemical analysis film can be good even if the second frameless chemical analysis film is spotted with the sample liquid by the same spotting tip as the first frameless chemical analysis film.

Further when a component of one of two frameless chemical analysis films can affect the measurement with the other frameless chemical analysis film, the accuracies of measurement with both the frameless chemical analysis films can be assured by spotting the sample liquid onto said the other frameless chemical analysis film before said one frameless chemical analysis film.

DESCRIPTION OF THE PREFERRED EMBODIMENT

Figure 1:
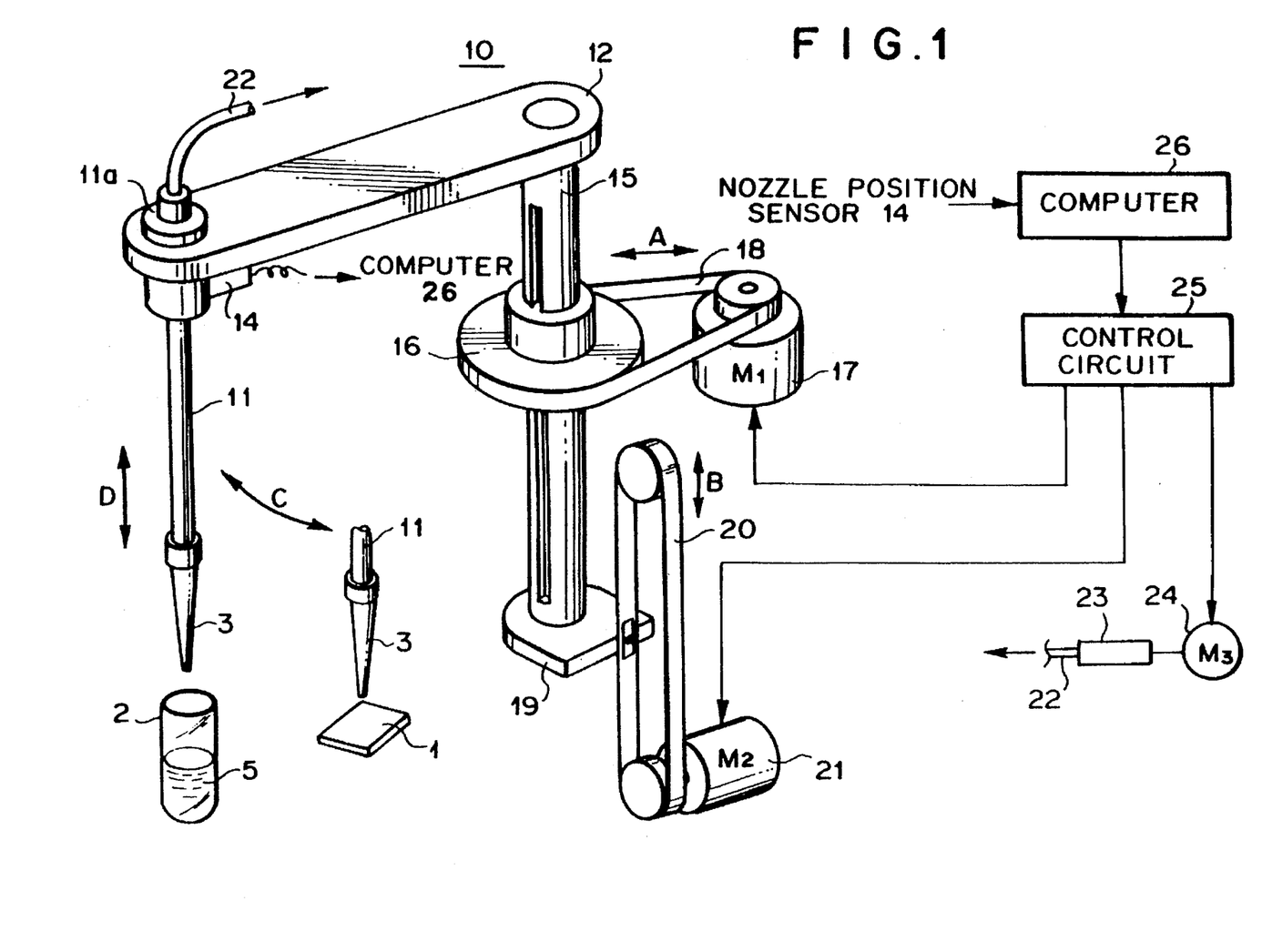
FIG. 1 is a schematic perspective view showing a spotting mechanism for carrying out the method of the present invention.

In FIG. 1, a spotting mechanism 10 for carrying out the method of the present invention spots a sample liquid 5 contained in a sample tube 2 onto a frameless chemical analysis film 1 and comprises a spotting nozzle 11 which sucks and discharges the sample liquid 5 and a spotting tip 3 in the form of a pipette which is removably mounted on the spotting nozzle 11. The spotting nozzle 11 sucks the sample liquid 5 into the spotting tip 3 and the spotting tip 3 is changed when the sample liquid 5 is changed.

The frameless chemical analysis film 1 comprises, for instance, a light-transmissive support sheet of an organic polymer or a plastic such as ployethylene terephthalate and a reagent layer and a spreading layer formed on the support sheet in this order. If necessary, a protective layer resistant to rubbing formed of a fibrous material may be laminated on the reagent layer or such a protective layer may be arranged to double as the spreading layer. It should be noted that the frameless chemical analysis film is not provided with any frame.

The reagent layer comprises at least one layer composed of a porous layer or hydrophilic polymer binder such as gelatin containing therein a detecting reagent component (chemical analysis reagent or immunoassay reagent) which is selectively reacts with analyte and a reagent component which is necessary for coloring reaction. Arrangements of frameless chemical analysis films for measuring LDH and GPT will be described later.

The frameless chemical analysis film 1 is apt to be warped, curled or curved toward the reagent layer in a dry state before use, and the degree of warp, curl or curve depends on the kind of the reagent layer and the dryness of the film 1.

Figure 2A:
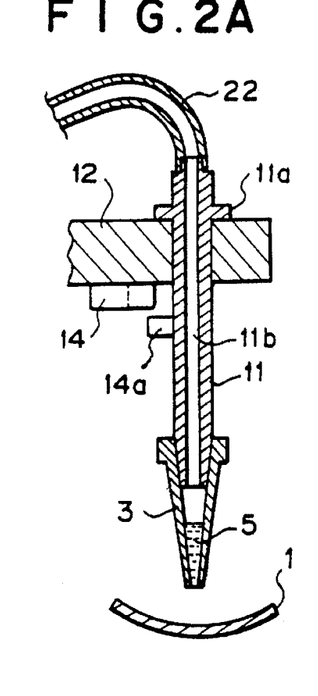
FIGS. 2A to 2C are fragmentary cross-sectional views for illustrating the procedure of spotting the sample liquid in accordance with an embodiment of the present invention.

The spotting nozzle 11 vertically extends through the free end portion of a horizontally extending sampling arm 12 and is supported by the sampling arm 12 to be slightly movable up and down. As shown in FIG. 2, the spotting nozzle 11 is supported on the sampling arm 12 with a flange portion 11a of the spotting nozzle 11 resting on the upper surface of the sampling arm 12. A nozzle position sensor (photosensor) 14 for detecting an up-and-down movement of the spotting nozzle 11 is mounted on the lower surface of the sampling arm 12. The nozzle position sensor 14 detects an up-and-down movement of the spotting nozzle 11 by way of a flag 14a affixed to the shank of the spotting nozzle 11.

The base end of the sampling arm 12 is fixed to the upper end portion of an erected spline shaft 15 and the sampling arm 12 is rotated about the spline shaft 15 integrally therewith. The spline shaft 15 extends through a pulley 16 to be rotated together with the pulley 16 and to be movable relative to the pulley 16 in the axial direction thereof and is supported to be movable up and down. A belt 18 is passed around the pulley 16 and a driving pulley of a first motor 17 and the first motor 17 drives the belt 18 as shown by arrow A to rotate the pulley 16, thereby swinging the spotting nozzle 11 by way of the spline shaft 15 and the sampling arm 12.

A connecting member 19 is fixed to the lower end of the spline shaft 15 and a belt 20 which is driven in a vertical direction as shown by arrow B by a second motor 21 is fixed to the connecting member 19. The second motor 21 moves up and down the spline shaft 15 by way of the belt 20, thereby moving up and down the spotting nozzle 11.

An air hose 22 is connected to the upper end of the spotting nozzle 11 and is communicated with the spotting tip 3 through an air passage 11b (FIG. 2) extending through the spotting nozzle 11. The air hose 22 is further connected to a pressure source or a syringe 23 whose piston rod is actuated by a third motor 24. A negative or positive pressure generated in the syringe 23 in response to actuation of the piston rod by the third motor 24 is applied to the spotting tip 3 through the air hose 22 to suck, hold or discharge the sample liquid 5.

The motors 17, 21 and 24 are controlled by a control circuit 25 and a computer 26 outputs a predetermined motor control signal to the control circuit 25 according to a predetermined sequence program when a detecting signal is input into the computer 26 from the nozzle position sensor 14.

Figure 2B:
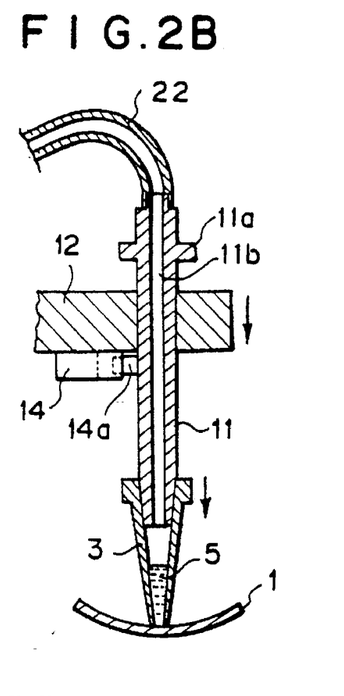
Figure 2C:
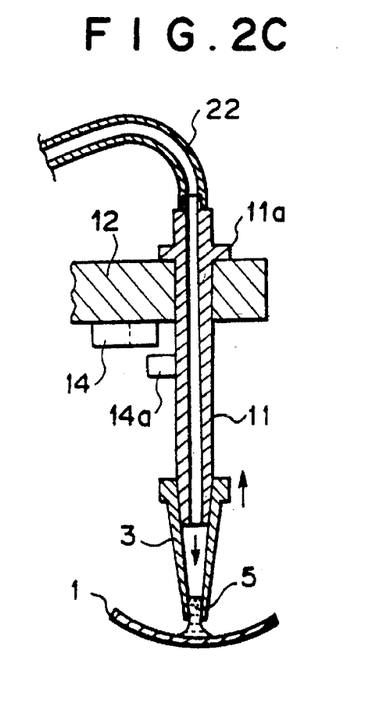

The spotting mechanism 10 spots the sample liquid 5 onto the frameless chemical analysis film 1 in the following manner. That is, the sampling arm 12 is lowered to drive the spotting tip 3 into the sample liquid 5 in the sample tube 2 and the sample liquid 5 is sucked into the spotting tip 3. Then the sampling arm 12 is lifted and rotated to bring the spotting tip 3 above a frameless chemical analysis film 1 in a spotting position. Then the sampling arm 12 is lowered to move the spotting tip 3 holding therein the sample liquid 5 toward the surface of the frameless chemical analysis film 1 as shown in FIG. 2A. When the end of the spotting tip 3 is brought into abutment against the frameless chemical analysis film 1, the spotting tip 3 is stopped there by the frameless chemical analysis film 1 (which is slightly deformed) while the sampling arm 12 is kept lowered leaving the spotting tip 3 and the spotting nozzle 11 there as shown in FIG. 2B. When the flag 14a on the spotting nozzle 11 is inserted into the slit of the nozzle position sensor 14, a light beam to the light receiving element of the nozzle position sensor 14 is interrupted by the flag 14a and the nozzle position sensor 14 detects that the end of the spotting tip 3 is in contact with the surface of the frameless chemical analysis film 1.

When contact of the spotting tip 3 with the film surface is detected, the sampling arm 12 is moved upward. At this time, the end of the spotting tip 3 is kept in contact with the frameless chemical analysis film 1 until the upper surface of the sampling arm 12 is brought into abutment against the flange 11a of the spotting nozzle 11. When the nozzle position sensor 14 is moved way from the flag 14a in response to the upward movement of the sampling arm 12, the light beam comes to enter the light receiving element of the nozzle position sensor 14 and the nozzle position sensor 14 detects that the end of the spotting tip is moving away from the surface of the frameless chemical analysis film 1.

The flag 14a is positioned relative to the nozzle position sensor 14 so that the flag 14a comes to permit the light beam to enter the light receiving element of the nozzle position sensor 14 substantially the instant the upper surface of the sampling arm 12 is brought into abutment against the flange 11a of the spotting nozzle 11, that is, so that the nozzle position sensor 14 detects that the end of the spotting tip is moving away from the surface of the frameless chemical analysis film 1 as soon as the spotting nozzle 11 comes to move upward together with the sampling arm 12. As the spotting tip 3 is moved upward together with the sampling arm 12, the sample liquid 5 in the spotting tip 3 is discharged onto the frameless chemical analysis film 1 at a predetermined rate. The spotting tip lifting speed and the sample liquid discharging speed are controlled according to the sample liquid spreading speed on the film surface, the viscosity of the sample liquid 5 and the like so that the discharged flow of the sample liquid does not break or the discharged sample liquid 5 does not stand up above the film surface to adhere to the end of the spotting tip 3.

When the same sample liquid 5 is to be spotted onto another frameless chemical analysis film 1 for a different analyte thereafter, the spotting nozzle 11 is returned to above the sample tube 2 and the spotting action described above is repeated. When a different sample liquid 5 is to be spotted thereafter, the spotting tip 3 used in the preceding spotting action is removed and a new spotting tip 3 is mounted on the spotting nozzle 11 and then the spotting action described above is repeated.

Figure 3:
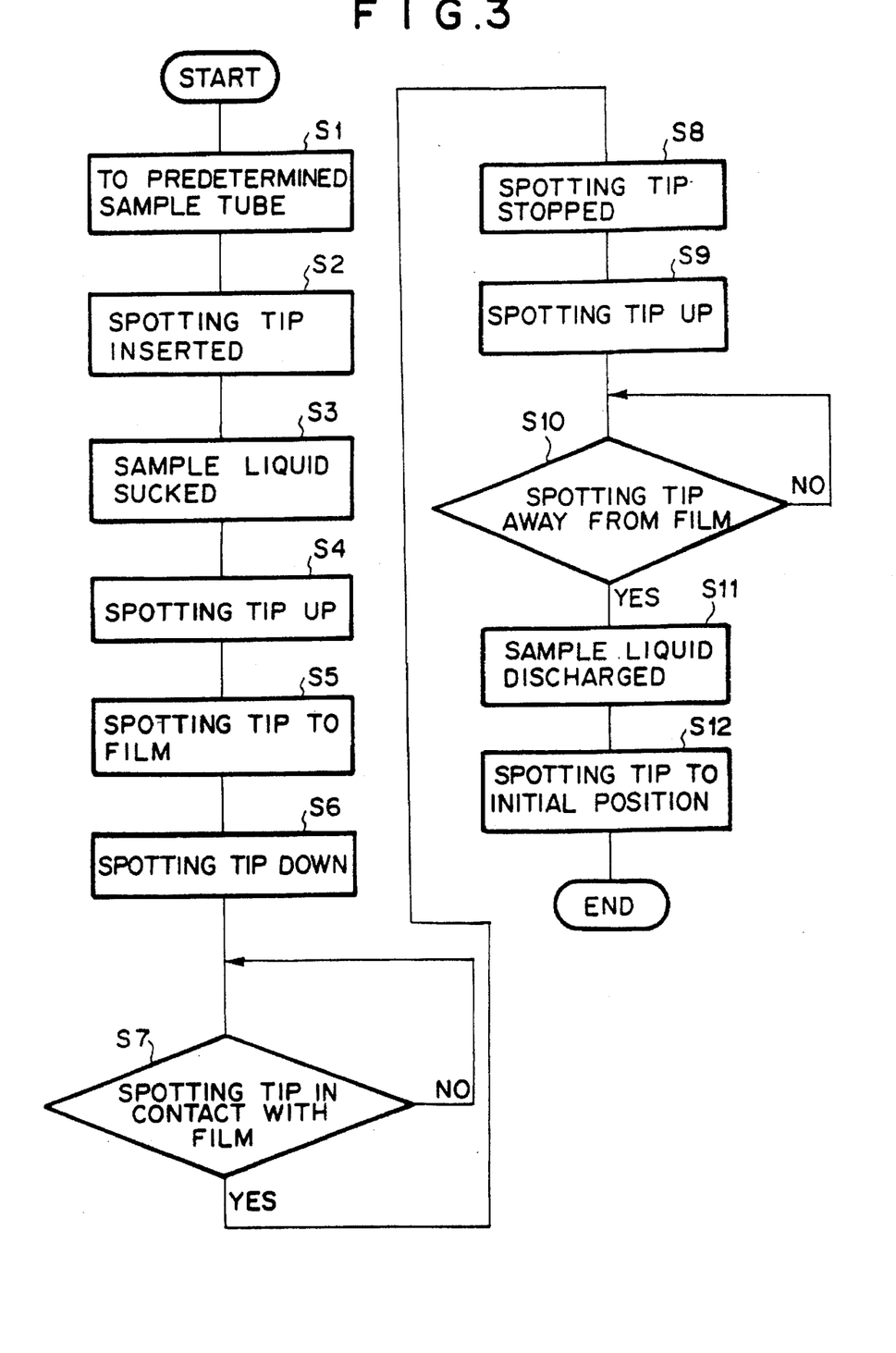
FIG. 3 is a flow chart for illustrating the sequence program of the computer.

The sequence program for the computer 26 will be described with reference to the flow chart shown in FIG. 3, hereinbelow. The computer 26 controls the control circuit 25 to output a predetermined motor drive signal to the first motor 17 to rotate the sampling arm 12 in the direction of arrow C in FIG. 1 to bring the spotting tip 3 above the sample tube 2. (step S1) Then the computer 26 controls the control circuit 25 to output a predetermined motor drive signal to the second motor 21 to lower the sampling arm 12 in the direction of arrow D to insert the end portion of the spotting tip 3 into the sample liquid 5 in the sample tube 2. (step S2) Then the computer 26 controls the control circuit 25 to output a predetermined motor drive signal to the third motor 24 to actuate the syringe 23. Actuation of the syringe 23 by a predetermined amount generates a negative pressure in the air hose 22, the air passage 11b in the spotting nozzle 11 and the spotting tip 3 and a predetermined amount of (slightly larger than the amount to be discharged) sample liquid 5 is sucked into the spotting tip 3. (step S3)

Then the computer 26 controls the control circuit 25 to output a predetermined motor drive signal to the second motor 21 to lift the sampling arm 12 and the spotting tip 3. (step S4) Thereafter the computer 26 controls the control circuit 25 to output a predetermined motor drive signal to the first motor 17 to rotate the sampling arm 12 to bring the spotting tip 3 above the frameless chemical analysis film 1 in the spotting position. (step S5)

The computer 26 then controls the control circuit 25 to output a predetermined motor drive signal to the second motor 21 to lower the sampling arm 12 and the spotting tip 3. (step S6) When a detecting signal representing that the end of the spotting tip 3 has been brought into contact with the film surface is input into the computer 26 from the nozzle position sensor 14, the computer 26 controls the control circuit 25 to output a predetermined motor drive signal to the second motor 21 to stop the second motor 21, thereby stopping the sampling arm 12. (steps S7 and S8) Then the computer 26 reverses the second motor 21 to move upward the sampling arm 12. (step S9)

When a detecting signal representing that the end of the spotting tip 3 has been moved away from the film surface is input into the computer 26 from the nozzle position sensor 14, the computer 26 controls the control circuit 25 to output a predetermined motor drive signal to the third motor 24 to actuate the syringe 23. Actuation of the syringe 23 generates a positive pressure in the air hose 22, the air passage 11b in the spotting nozzle 11 and the spotting tip 3 and the sample liquid 5 in the spotting tip 3 is discharged on the frameless chemical analysis film 1 at a predetermined rate. (steps S10 and S11)

Thereafter the computer 26 controls the control circuit 25 to output predetermined motor drive signals to the first and second motors 17 and 21 to return the spotting tip 3 to the initial position for the next spotting action.

The rotating speeds of the second and third motors 21 and 24 are controlled according to the speed at which the sample liquid 5 spreads on the film surface and the viscosity of the sample liquid 5 so that the speed at which the sampling arm 12 is moved upward in step S9 and the rate at which the sample liquid is discharged in step S11 are such that the discharged flow of the sample liquid does not break or the discharged sample liquid 5 does not stand up above the film surface to adhere to the end of the spotting tip 3.

For example, the sample liquid 5 is blood plasma and the frameless chemical analysis film 1 is for analysis of LDH, the rotating speeds of the second and third motors 21 and 24 are controlled so that the sampling arm 12 is moved upward at 0.6 mm/sec in step S9 and the sample liquid is discharged at 27 μL/sec in step S11.

Though in this embodiment that the spotting tip 3 is brought into contact with the frameless chemical analysis film 1 is detected by the nozzle position sensor 14 and the nozzle lifting speed and the sample liquid discharging rate (or timing) are controlled on the basis of the detection, such a nozzle position sensor 14 need not be used. For example, when a discharging pressure is applied while lifting the sampling arm 12 after the spotting tip 3 is stopped in the position shown in FIG. 2B, the sample liquid 5 is not discharged until the end of the spotting tip 3 is moving away from the film surface.

A method of spotting a sample liquid in accordance with another embodiment of the present invention will be described with reference to FIGS. 4A to 4E, hereinbelow. In this embodiment, a small amount of air is further sucked into the spotting tip 3 after the sample liquid 5 is sucked into the spotting tip 3, whereby air is trapped in the end portion of the spotting tip 3.

Figure 4A:
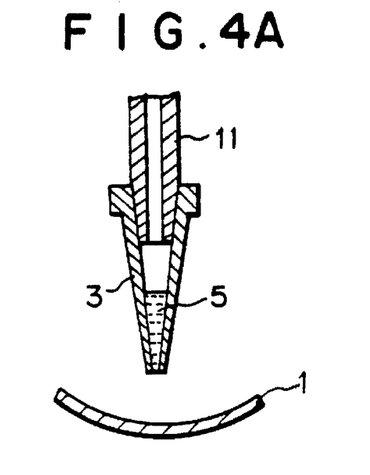
FIGS. 4A to 4E are fragmentary cross-sectional views for illustrating the procedure of spotting the sample liquid in accordance with another embodiment of the present invention.
Figure 4B:
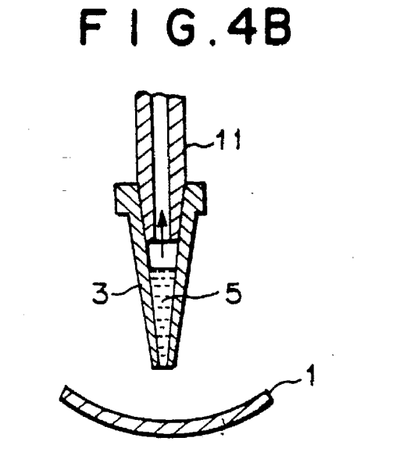

That is, in this embodiment, the spotting tip 3 holding therein the sample liquid 5 is moved to just above the frameless chemical analysis film 1 as shown in FIG. 4A. Then the syringe 23 is actuated to suck a small amount of air so that a small amount of air is trapped in the end portion of the spotting tip 3 below the sample liquid 5 as shown in FIG. 4B.

Figure 4C:
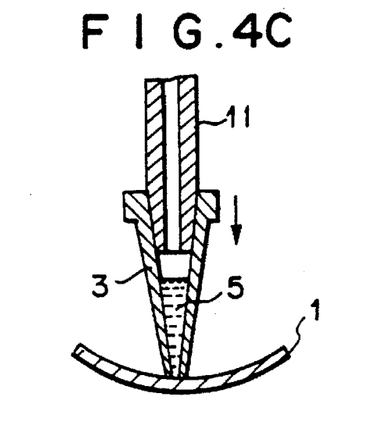
Figure 4D:
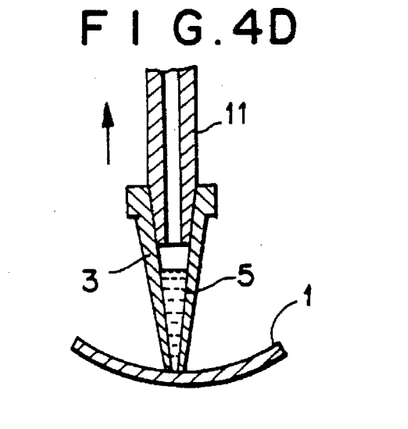

Then the spotting tip 3 is lowered and brought into contact with the frameless chemical analysis film 1 as shown in FIG. 4C. Then in response to detection of contact of the spotting tip 1 with the film surface, the spotting tip 3 is moved upward as shown in FIG. 4D and at the same time a positive pressure is applied to the air passage 11b in the spotting nozzle 11 to start discharging the sample liquid 5.

Figure 4E:
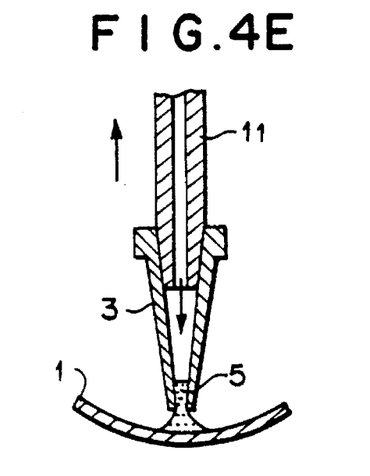

However since air is in the end portion of the spotting tip 3, air is first discharged when the end of the spotting tip 3 is moved away from the film surface and the sample liquid 5 is not discharged from the spotting tip 3 until the end of the spotting tip 3 is moved away from the film surface by a predetermined distance as shown in FIG. 4E. Thereafter as the spotting tip 3 is lifted, the sample liquid 5 in the spotting tip 3 is discharged at a predetermined rate.

In this embodiment, the air trapped in the end portion of the spotting tip 3 prevents the end of the spotting tip 3 from contacting the film surface wet with the sample liquid 5, whereby the amount of substances transferred to the end of the spotting tip 3 from the frameless chemical analysis film 1 can be reduced.

The method of the present invention may be variously modified without limited to those described above. For example, that the end of the spotting tip 3 is brought into contact with the film surface may be detected by use of a reflective photosensor 28 shown in FIGS. 5A and 5B instead of the nozzle position sensor 14 described above.

Figure 5A:
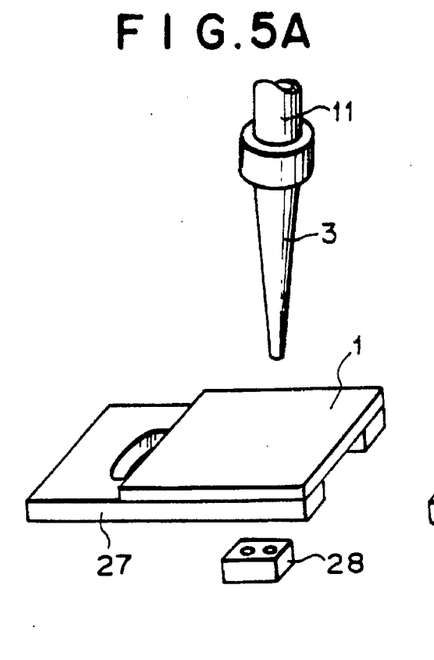
FIGS. 5A and 5B are fragmentary perspective views for illustrating a modification of the sensor for detecting contact of the spotting tip with the frameless chemical analysis film.
Figure 5B:
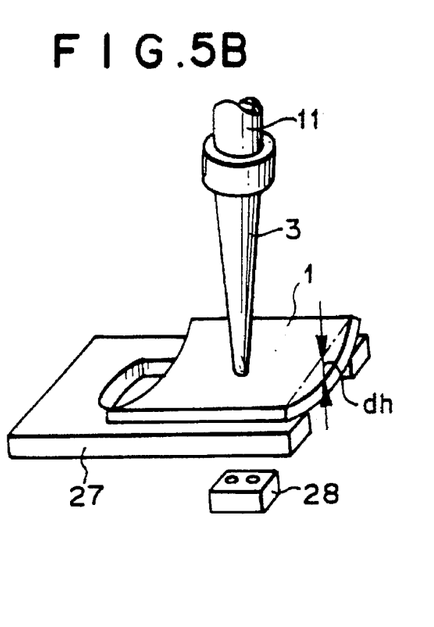

That is, in FIGS. 5A and 5B, the frameless chemical analysis film 1 is placed on a horseshoe-shaped transfer member 27 and when the film 1 is pushed by the end of the spotting tip 3, the film 1 is deformed to be convex downward as shown in FIG. 5B. The reflective photosensor 28 is set so that its output is maximized when the object is at a predetermined distance therefrom. The output of the photosensor 28 when the frameless chemical analysis film 1 is free and in a non-deformed state shown in FIG. 5A differs from that when the frameless chemical analysis film 1 is deformed by the spotting tip 3 as shown in FIG. 5B by a value corresponding to the difference dh in the distance from the lower surface of the film 1 to the photosensor 28 between the former state and the latter state. That the end of the spotting tip 3 is brought into contact with the film surface is detected on the basis of the change in the output of the reflective photosensor 28.

Figure 6:
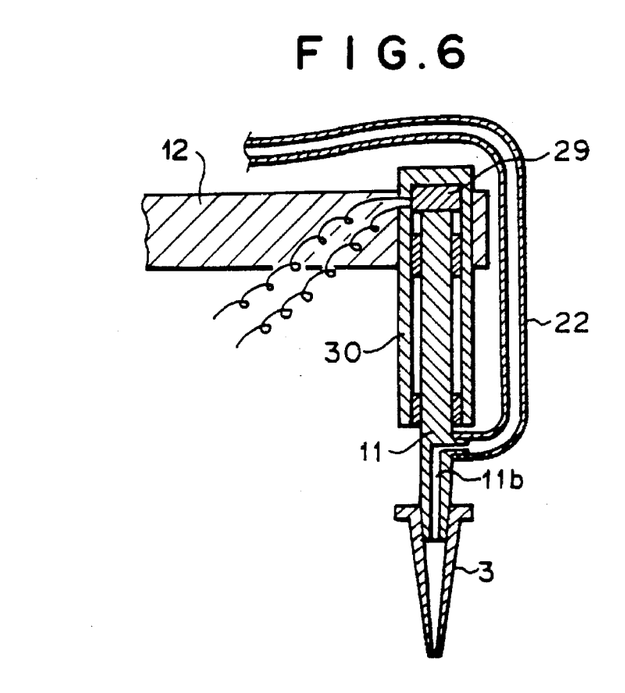
FIG. 6 is a fragmentary perspective view for illustrating another modification of the sensor for detecting contact of the spotting tip with the frameless chemical analysis film.

That the end of the spotting tip 3 is brought into contact with the film surface may otherwise be detected by use of a pressure sensor 29 disposed on the top of the spotting nozzle 11 which is supported on the sampling arm 12 to be displaced in the axial direction of thereof as shown in FIG. 6.

The pressure sensor 29 and the upper end portion of the spotting nozzle 11 are housed in a cover 30 and when the end of the spotting tip 3 is brought into contact with the frameless chemical analysis film 1, the pressure transmitted to the pressure sensor 29 from the spotting nozzle 11 increases. Thus the contact of the spotting tip 3 with the film surface can be detected through the change in the output signal of the pressure sensor 29. In this case, it is preferred that the air hose 22 be connected to the air passage 11b in the spotting nozzle 11 through the side wall of the spotting nozzle 11.

Further the spotting tip lifting speed and the sample liquid discharging rate may be changed in a predetermined pattern.

The order of spotting a sample liquid onto a plurality of frameless chemical analysis films 1 will be described hereinbelow. In the method of the present invention, when a sample liquid 5 is spotted onto a plurality of frameless chemical analysis films 1 for different analytes with a spotting tip 3, the spotting order is properly set so that a component of a frameless chemical analysis film 1 spotted earlier does not affect analysis with a frameless chemical analysis film 1 spotted later.

That is, when a first frameless chemical analysis film 1 includes a component which can be transferred to a second frameless chemical analysis film 1 by way of the spotting tip 3 and can deteriorate the accuracy of measurement of the analyte for the second frameless chemical analysis film 1, the sample liquid 5 is spotted, before the second frameless chemical analysis film 1 after the first frameless chemical analysis film 1, onto a third frameless chemical analysis film 1 the analyte of which is not such that the accuracy of its measurement is substantially affected by a component of the first frameless chemical analysis film 1 which can be transferred to the third frameless chemical analysis film 1 from the first frameless chemical analysis film 1 by way of the spotting tip 3.

For example, when the first frameless chemical analysis film 1 is for LDH and the second frameless chemical analysis film 1 is for GPT, the spotting order is set so that the film 1 for GPT is not spotted immediately after spotting the film 1 for LDH and, for instance, a film 1 for TCHO (total cholesterol) is spotted prior to the film 1 for GPT. As can be understood from the result of the experiment to be described later, the number of the frameless chemical analysis films to be spotted between the first and second frameless chemical analysis films 1 may be one or more.

Further, error in measurement of GPT can be prevented also by spotting the film 1 for GPT prior to the film 1 for LDH.

The frameless chemical analysis film 1 for LDH comprises, for instance, a transparent support sheet of polyethylene terephthalate, and a water absorbing layer and a spreading layer formed on the support sheet. The spreading layer contains therein reagent composition including lactate, $NAD^+$, sodium glutamate, diaphorase, NTB, GPT and the like. (See Japanese Unexamined Patent Publication No. 62(1987)-205798 (DE 3707110 A), especially embodiment 1)

When a sample liquid 5 is spotted onto the film 1 for LDH, LDH reacts with the reagent in the following manner and the amount of coloring substance generated by the reaction is measured. When GPT contained in the reagent in order to remove inhibitor is transferred to the frameless chemical analysis film 1 for GPT by way of the spotting tip 3, the accuracy of measurement with the film 1 for GPT is affected.

(1)

(2)

(3)

NAD$^+$ (coloring reaction)

The frameless chemical analysis film 1 for GPT comprises, for instance, a transparent support sheet of polyethylene terephthalate, and a coloring reagent layer, an adhesive layer and a spreading layer formed on the support sheet. The coloring reagent layer contains therein reagent components such as Leuco dye, peroxidase and the like, and the spreading layer contains therein a reagent composition including L-alanine, α-ketoglutaric acid, phosphate and the like. (See Japanese Unexamined Patent Publication No. 62(1987)-79362, especially embodiment 1)

When a sample liquid 5 is spotted onto the film 1 for GPT, GPT reacts with the reagent in the following manner and the amount of coloring substance generated by the reaction is measured.

(1)

(2)

(3)

As can be understood from the reaction formulae above, the frameless chemical analysis film 1 for quantitative analysis of LDH contains GPT which is the analyte of the frameless chemical analysis film 1 for quantitative analysis of GPT. Accordingly, GPT is apt to adhere to the end of the spotting tip 3 when the spotting tip 3 is brought into contact with the frameless chemical analysis film 1 for LDH in the spotting action on the frameless chemical analysis film 1 for LDH. Accordingly when the spotting tip 3 is brought into contact with the frameless chemical analysis film 1 for GPT in the spotting action on the frameless chemical analysis film 1 for GPT, GPT is apt to be transferred to the frameless chemical analysis film 1 for GPT from the frameless chemical analysis film 1 for LDH by way of the spotting tip 3, which results in a larger value of the measured GPT content than the actual GPT content in the sample liquid 5.

EXAMPLE

Figure 7A:
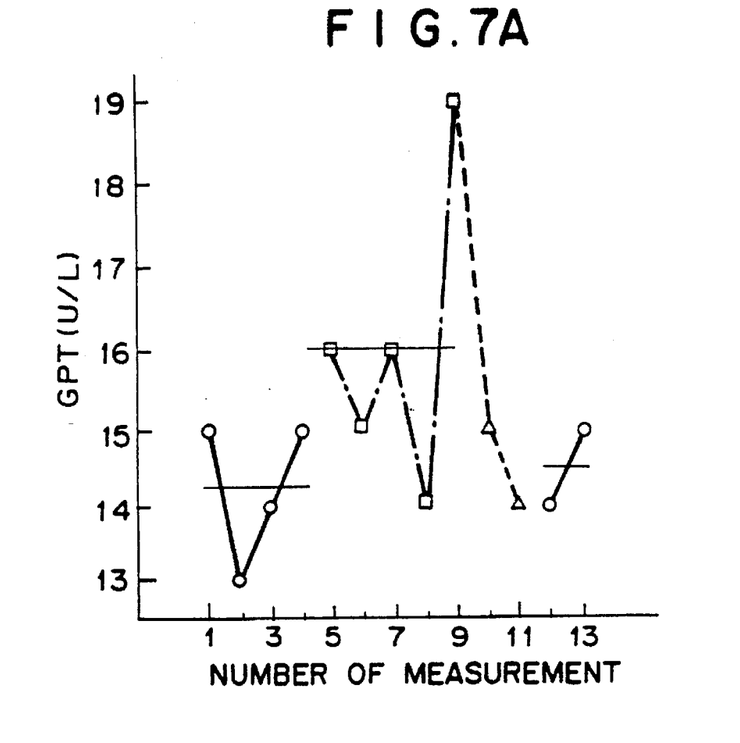
FIGS. 7A and 7B are graphs showing the result of experiment for investigating influence of the spotting order on the measured values.
Figure 7B:
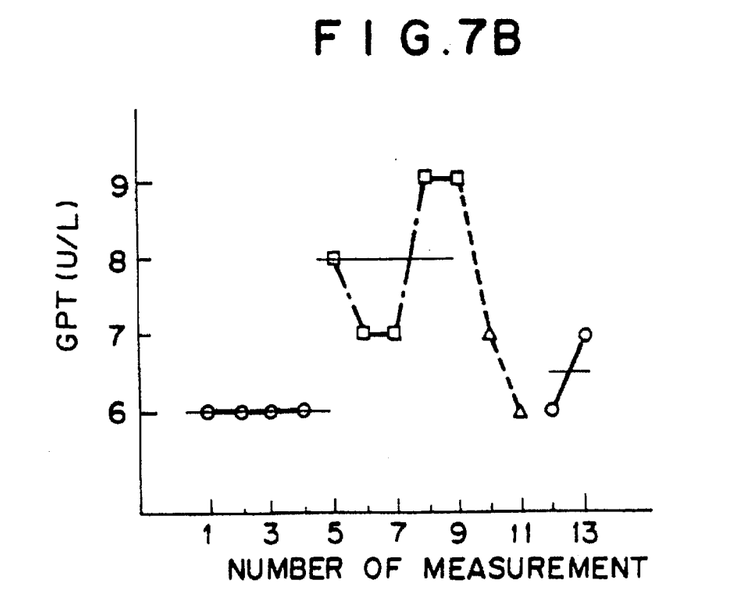

Influence on the accuracy of measurement of GPT of spotting the frameless chemical analysis film for GPT after spotting the frameless chemical analysis film 1 for LDH with the same spotting tip was investigated in the following manner and the result is shown in FIGS. 7A and 7B. Spotting was effected in the manner described above in conjunction with FIGS. 4A to 4E by use of an automated spotting mechanism.

Measurement 1:

Four frameless chemical analysis films for GPT were spotted with 10 µL of reference liquid in sequence and measured values without contamination were obtained. Another four frameless chemical analysis films for GPT were spotted with 5 µL of reference liquid in sequence and measured values without contamination were obtained. The measured values of GPT (No.1 to NO.4) for 10 µL and 5 µL are shown by ○ in FIGS. 7A and 7B, respectively.

Measurement 2:

Five frameless chemical analysis films for GPT were spotted with 10 µL of the same reference liquid each after spotting the frameless chemical analysis film for LDH and measured values with contamination were obtained. Another five frameless chemical analysis films for GPT were spotted with 5 µL of the same reference liquid each after spotting the frameless chemical analysis film for LDH and measured values with contamination were obtained. The measured values of GPT (No.5 to NO.9) for 10 µL and 5 µL are shown by □ in FIGS. 7A and 7B, respectively.

Measurement 3:

After spotting the last frameless chemical analysis film in the measurement 2, a pair of frameless chemical analysis films for GPT were spotted in sequence to investigate continuity of contamination. The measured values of GPT (No.10 and 11) for 10 µL and 5 µL are shown by Δ in FIGS. 7A and 7B, respectively.

Measurement 4:

After effecting measurements 1 to 3 with the same spotting tip, the spotting tip was changed and a pair of frameless chemical analysis films for GPT were spotted in sequence with a new spotting tip. The measured values of GPT (No.12 and 13) for 10 µL and 5 µL are shown by ○ in FIGS. 7A and 7B, respectively.

As can be understood from FIGS. 7A and 7B, the measured values with contamination (measurement 2) are larger than those without contamination (measurement 1 and measurement 4) by about 1.5 to 2 U/L on the average, which clearly indicates influence of GPT transferred by way of the spotting tip 3. However, the result of measurement 3 shows that the influence of GPT transferred by way of the spotting tip 3 becomes negligible in the frameless chemical analysis film spotted second after spotting of the frameless chemical analysis film for LDH. (The measured value of No. 11 is substantially equal to those in measurement 1 and measurement 4) Accordingly, by spotting only one third frameless chemical analysis film after spotting the frameless chemical analysis film for LDH before spotting the frameless chemical analysis film for GPT, the problem of contamination can be avoided.

The GPT content of the reagent layer of the frameless chemical analysis film for LDH was 4.2 mU/mm$^2$ and the area of contact of the spotting tip 3 was 0.59 mm$^2$. Assuming that the whole contact area transfers GPT, 250 U/L of GPT is transferred. Actually, the amount of transferred GPT was 2 U/L which was 1/125.

Other examples of combination of frameless chemical analysis films which can gives rise to the problem of contamination are as follows, and in these combinations, the spotting order should be selected in the manner described above.

1. Spotting of a frameless chemical analysis film for IP (inorganic phosphorous) after that of a frameless chemical analysis film for TCHO (total cholesterol).
2. Spotting of a frameless chemical analysis film for UA (uric acid) after that of a frameless chemical analysis film for TCHO.
3. Spotting of a frameless chemical analysis film for IP after that of a frameless chemical analysis film for GPT.
4. Spotting of a frameless chemical analysis film for GOT (glutamic-oxaloacetic transaminase, or aspartate aminotransferase) after that of a frameless chemical analysis film for GPT.
5. Spotting of a frameless chemical analysis film for GGT or γGTP (γ-glutamyl transpeptitase) after that of a frameless chemical analysis film for ALP (alkaline phosphatase).

What is claimed is:

1. In a method for spotting a sample liquid onto a plurality of frameless chemical analysis films for purposes of analyzing an analyte in the sample liquid wherein a predetermined amount of the sample is sucked into a spotting tip of a spotting nozzle, the spotting tip is lowered to bring a lower end of the spotting tip into contact with a surface of each frameless film and pressure inside the spotting tip is increased to discharge the sample liquid therein onto the surface of the analysis film while lifting the spotting tip away from the surface of the film, a first frameless chemical analysis film including a component which is transferrable to a second frameless film by the spotting tip and can decrease the accuracy of measurement of an analyte in the sample liquid to be analyzed by the second analysis film, the improvement comprising prior to spotting the liquid sample onto the second film, spotting the liquid sample onto a third frameless chemical analysis film which does not include a component which is transferrable to the second analysis film by the spotting tip and which can decrease the accuracy of measurement of the analyte to be measured by the second analysis film, and wherein the analyte to be measured on the third analysis film is one whose measurement is not substantially affected by the transferrable component.

2. A method as defined in claim 1 in which said first frameless chemical analysis film is for analysis of lactate dehydrogenase and the second frameless chemical analysis film is for analysis of glutamic-pyruvic transaminase.

3. A method as defined in claim 1 in which said first frameless chemical analysis film is for analysis of total cholesterol and the second frameless chemical analysis film is for analysis of inorganic phosphorous.

4. A method as defined in claim 1 in which said first frameless chemical analysis film is for analysis of total cholesterol and the second frameless chemical analysis film is for analysis of uric acid.

5. A method as defined in claim 1 in which said first frameless chemical analysis film is for analysis of glutamic-pyruvic transaminase and the second frameless chemical analysis film is for analysis of inorganic phosphorous.

6. A method as defined in claim 1 in which said first frameless chemical analysis film is for analysis of glutamic-pyruvic transaminase and the second frameless chemical analysis film is for analysis of glutamic-oxaloacetic transaminase.

7. A method as defined in claim 1 in which said first frameless chemical analysis film is for analysis of alkaline phosphatase and the second frameless chemical analysis film is for analysis of γ-glutamyl transpeptitase.

* * * * *